United States Patent
Reger

(10) Patent No.: US 7,454,987 B2
(45) Date of Patent: Nov. 25, 2008

(54) APPARATUS AND METHOD FOR DETERMINING A POSITION OF A PATIENT IN A MEDICAL EXAMINATION

(75) Inventor: Johannes Reger, Erbendorf (DE)

(73) Assignee: Siemens Aktiengesellschaft, Munich (DE)

( * ) Notice: Subject to any disclaimer, the term of this patent is extended or adjusted under 35 U.S.C. 154(b) by 106 days.

(21) Appl. No.: 11/211,959

(22) Filed: Aug. 25, 2005

(65) Prior Publication Data

US 2006/0193443 A1 Aug. 31, 2006

(30) Foreign Application Priority Data

Aug. 30, 2004 (DE) ........................ 10 2004 041 897

(51) Int. Cl.
*A61B 6/00* (2006.01)
(52) U.S. Cl. ........................ 73/862.474; 378/209; 5/601; 5/943
(58) Field of Classification Search ................. 73/1.13, 73/1.15, 862.474, 862.473, 862.472, 862.46, 73/862.391, 862.381; 378/20, 208, 209; 5/601, 593; 382/131
See application file for complete search history.

(56) References Cited

U.S. PATENT DOCUMENTS

| | | | | |
|---|---|---|---|---|
| 3,757,065 | A * | 9/1973 | Eberle et al. | 200/85 A |
| 4,125,907 | A * | 11/1978 | Junginger et al. | 5/87.1 |
| 4,311,980 | A * | 1/1982 | Prudenziati | 338/4 |
| 4,506,250 | A * | 3/1985 | Kirby | 338/5 |
| 4,802,801 | A * | 2/1989 | Fengler | 409/168 |
| 4,869,266 | A * | 9/1989 | Taylor et al. | 600/587 |
| 5,079,535 | A * | 1/1992 | Neuman et al. | 338/2 |
| 5,086,785 | A * | 2/1992 | Gentile et al. | 600/595 |
| 5,739,757 | A * | 4/1998 | Gioutsos | 340/667 |
| 6,208,250 | B1* | 3/2001 | Dixon et al. | 340/573.1 |
| 7,065,813 | B2* | 6/2006 | Hoth et al. | 5/601 |
| 7,110,494 | B2* | 9/2006 | Groh et al. | 378/95 |
| 2002/0081008 | A1* | 6/2002 | Wollenweber | 382/131 |
| 2002/0122575 | A1* | 9/2002 | Vaisburd et al. | 382/131 |
| 2004/0057557 | A1* | 3/2004 | Nafstadius | 378/209 |

FOREIGN PATENT DOCUMENTS

JP 10014911 * 1/1998

OTHER PUBLICATIONS

Patent Abstract of Japan, Inoue et al., Jan. 20, 1998, JP 10-014911.*
The Illustrated Dictionary of Electronics, 5th Ed., McGraw-Hill, Copyright 2001., pp. 236 and 659.*

* cited by examiner

*Primary Examiner*—Edward Lefkowitz
*Assistant Examiner*—Punam Patel
(74) *Attorney, Agent, or Firm*—Brinks, Hofer, Gilson & Lione

(57) ABSTRACT

An apparatus and a method are provided for determining a position of a patient during medical examinations. The apparatus comprises a tabletop operable to support the patient, at least one elongatable strain gauge which is integrated into the tabletop, and tabletop sensors operable to detect a sagging of the tabletop as a function of a change in length of the at least one elongatable strain gauge due to the sagging.

19 Claims, 3 Drawing Sheets

APPARATUS AND METHOD FOR DETERMINING A POSITION OF A PATIENT IN A MEDICAL EXAMINATION

FIELD

The present embodiments relate, in general, to medical examination systems, and in particular, to an apparatus and a method for determining a position of a patient in medical examinations.

BACKGROUND

Devices used in medical examinations are increasingly distinguished by substantially high accuracy and good quality of images. To provide substantially high-resolution images and optional image quality, an accurate location of a region of a patient to be examined, and hence of the patient, needs to meet increasingly stringent demands or requirements. There is, accordingly, a need for providing a suitable apparatus and a method by which a substantially accurate position of the patient during the medical examinations is determined.

In known medical systems, tabletops on which the patients are supported during the examinations are typically built or manufactured to be quite rigid, in order to minimize deformation and hence changes in the position of the patient. A disadvantageous aspect of this tabletop rigidity, however, is that deformations cannot be precluded in every case, which is unappreciatively imprecise because of the increased demands made of the images. Moreover, tabletops that are substantially hard or thick are a hindrance when making images.

Further, a sagging of the tabletop caused by the patient's weight may need to be determined to adjust the making of images or to adapt the images accordingly. Typically, this sagging of the tabletop was determined by weighing the patient and by constant and repeated measurements of the patient's location during the imaging process. However, this patient weighting and repetitive location measurements can be quite complicated and impractical.

BRIEF SUMMARY

The present embodiments are defined by the appended claims. This summary describes some aspects of the present embodiments and should not be used to limit the claims.

An apparatus and a method for determining a position of a patient during medical examinations can be accurate, simple to implement, and may not affect either an image to be taken or an image quality.

An apparatus for determining a position of a patient during medical examinations, includes a tabletop for supporting the patient; at least one elongatable strain gauge integrated into the tabletop; and sensors for detecting a sagging of the tabletop as a function of a length of the strain gauge that has elongated due to the sagging.

A method for determining a position of a patient during medical examinations includes the following steps: providing a tabletop for supporting a patient; integrating at least one elongatable strain gauge into the tabletop; and detecting a sagging of the tabletop as a function of a length of the strain gauge elongated due to the sagging.

By using strain gauges, which change in length in accordance with the sagging of the table, and sensors whose data serve to calculate the sagging of the tabletop, a simple and accurate method and apparatus are provided for determining the position of the patient with a substantially high resolution. Due to the provided apparatus, a quality of the images made by medical examination devices is not adversely affected, since there is no longer a need for a rigid and unyielding tabletop.

In one aspect, the strain gauge is integrated into the tabletop in a longitudinal direction of the tabletop. The strain gauge comprises electrically conductive material. Advantageously, the change in length of the strain gauge is detected via a change in an electrical resistance of the strain gauge.

Furthermore, the sensors are advantageously mounted on longitudinal ends of the strain gauge. A data processing device can calculate the sagging of the tabletop based on data measured by the sensors.

The tabletop is secured to a pedestal. In another aspect, pedestal sensors detect forces acting on the pedestal due to the sagging. Advantageously, a correlation between the data measured by the sensors and the pedestal sensors is stored in memory in a data processing device. In still another aspect, the data processing device calculates the sagging of the tabletop based on the data measured by the pedestal sensors and the correlation stored in memory.

Illustrative and exemplary embodiments are described in further detail below with reference to, and in conjunction with, the figures.

DETAILED DESCRIPTION

Figure 1A:
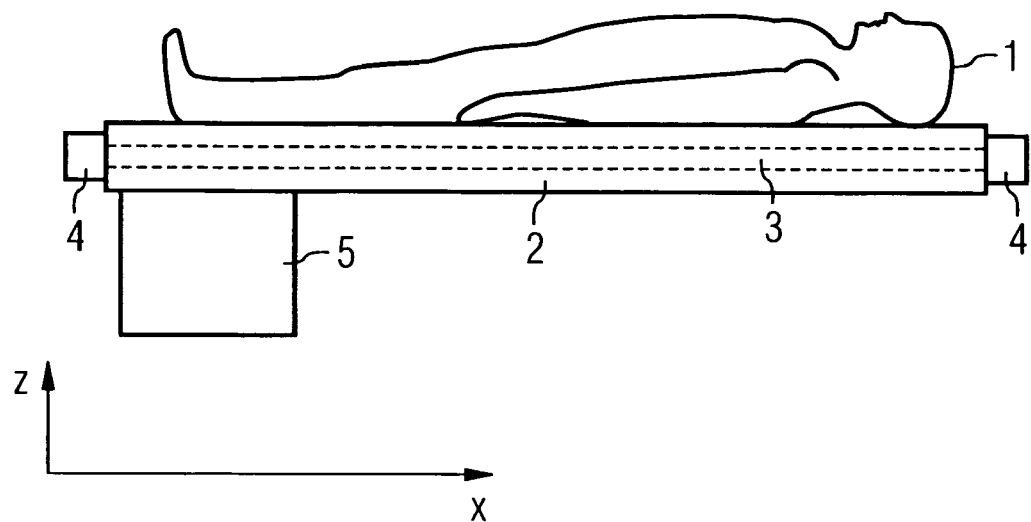
FIGS. 1A and 1B show side views of exemplary embodiments of the apparatus for determining a position of a patient during medical examinations.
Figure 1B:
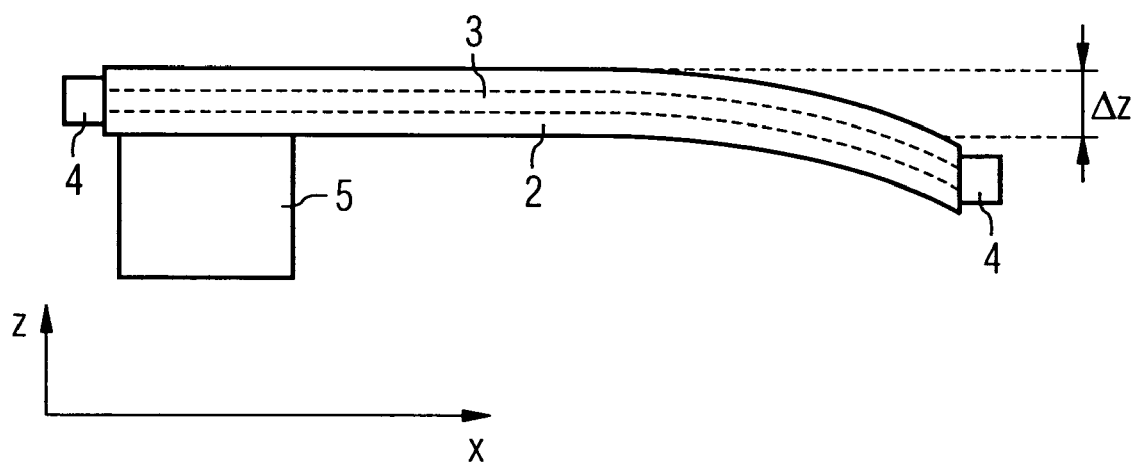

FIGS. 1A and 1B show side views of an apparatus with a tabletop 2 on which a patient 1 can be supported for the sake of a medical examination. A material used to manufacture the tabletop 2 is configured to suit the examination technique employed. At least one strain gauge 3 is integrated with the tabletop 2. The at least one strain gauge 3 extends in the longitudinal direction of the tabletop 2, but may also have different orientations, such as transversely to the longitudinal direction or vertically. A plurality of strain gauges, with similar or different orientations, may be integrated into the tabletop 2. For the sake of better understanding, the longitudinal direction of the tabletop is identified by the X-axis of a coordinate system, and a vertical direction of the tabletop is identified by the Z-axis of the coordinate system, as shown in FIGS. 1A and 1B. The weight of the patient 1 causes a sagging $\Delta Z$ of the tabletop 2, as shown in FIG. 1B. The strain gauge 3 integrated in the X direction of the tabletop 2 elongates when the tabletop sags, and the change in length of the strain gauge 3 is proportional to the sagging $\Delta Z$ of the tabletop 2. The more the tabletop sags, the greater the change in length of the strain gauge 3.

The strain gauge 3 may comprise a thin elongatable wire or any other elongatable electrically conductive material. Sensors 4 are mounted on longitudinal ends of the strain gauge 3. These sensors 4 may serve to measure the electrical resistance of the strain gauge 3. Since the electrical resistance of the strain gauge 3 changes with the length of the strain gauge 3, the change in the electrical resistance, and thus the change in length and as a result the sagging ΔZ of the tabletop, can be determined via the sensors 4.

Via strain gauge 3, the sagging of the tabletop 2 in one direction can be measured. As such, additional strain gauges 3 with different orientations into the tabletop 2 may be integrated, or a number of strain gauges 3 may be increased, to enable a more-detailed evaluation of points at which the sagging of the tabletop 2 is significant. In accordance with the number of strain gauges 3, a plurality of sensors 4 may also be integrated into the apparatus for detecting the electrical resistance of each individual strain gauge 3.

Figure 2:
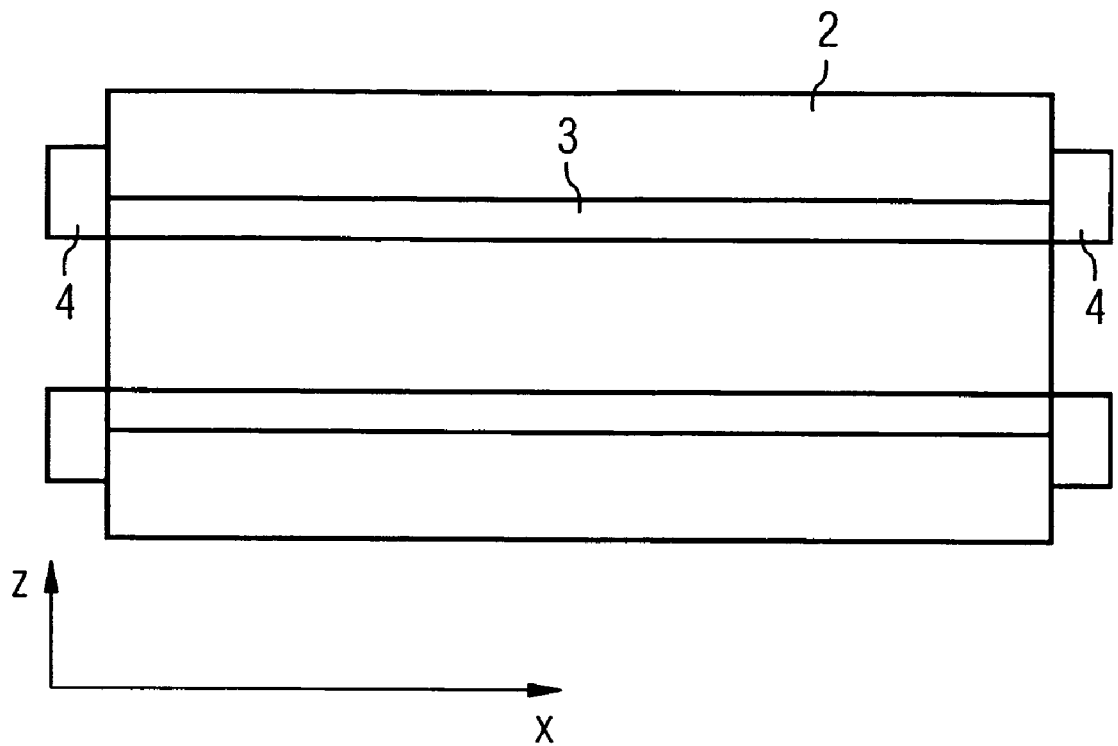
FIG. 2 is a plan view of the apparatus of FIGS. 1A and 1B.

FIG. 2 shows a plan view on the apparatus with the tabletop 2 and two strain gauges 3 integrated into the tabletop 2 with a sensor 4 mounted on each of the ends of the strain gauges 3. In analogy to FIGS. 1A and 1B, the longitudinal direction of the table is represented here by the X-axis of a coordinate system, and the transverse vertical direction of the tabletop 2 is represented by the Z-axis of the coordinate system.

As shown in FIGS. 1A and 1B, the tabletop 2 may be fastened to a pedestal 5 toward one end. Below, an example calculation of the sagging from the elongation measured is provided with the tabletop secured toward the pedestal side as an example.

A bending moment $M_b(x)$ exerted on the tabletop 2 by the weight of the patient 1 can be calculated as follows:

$$M_b(x) = \frac{q \times \chi^2}{2}$$

in which q is a linear load and χ is a corresponding coordinate on the X-axis. The units, the linear load is shown in N/mm units. The position of the tabletop along the equation:

$$z(x) = \frac{M_b \times x}{2 \times E_{Tischplatte} \times I_{Tischplatte}}$$

$$z(x) = \frac{M_b \times x}{2 \times E_{Tischplatte} \times I_{Tischplatte}}$$

$$z(x) = \frac{M_b \times x}{2 \times E_{Tischplatte} \times I_{Tischplatte}}$$

in which $E_{Tabletop}$ is a modulus of elasticity of the tabletop in N/mm² units, and $I_{Tabletop}$ is a moment of inertia per unit of surface area of the tabletop in mm⁴ units. A tension in the tabletop, $\sigma_{Tabletop}$, is calculated on one hand as follows:

$$\sigma_{Tabletop} = \frac{M_b(\chi)}{W_b(\chi)}$$

and on another hand as follows:

$$\sigma_{Tabletop} = E_{Tabletop} \times \epsilon_{Tabletop}$$

in which $W_b$ is a resistance moment of the tabletop, measured in mm³ units, and $\epsilon_{tabletop}$ is an elongation of the tabletop, which can be determined from the data, measured by the sensors 4, on the change in length of the strain gauge 3. After conversion, a resultant equation for the position of the tabletop is as follows:

$$z(x) = \frac{\sigma_{Tabletop} \times W_b \times \chi}{2 \times E_{Tabletop} \times I_{Tabletop}}$$

and after further conversion, as follows:

$$z(x) = \frac{\epsilon_{Tabletop} \times W_b \times \chi}{2 \times E_{Tabletop}^2 \times I_{Tabletop}}$$

as a result of which the sagging of the tabletop can be calculated as a function of the elongation measured with the strain gauges 3.

Figure 3:
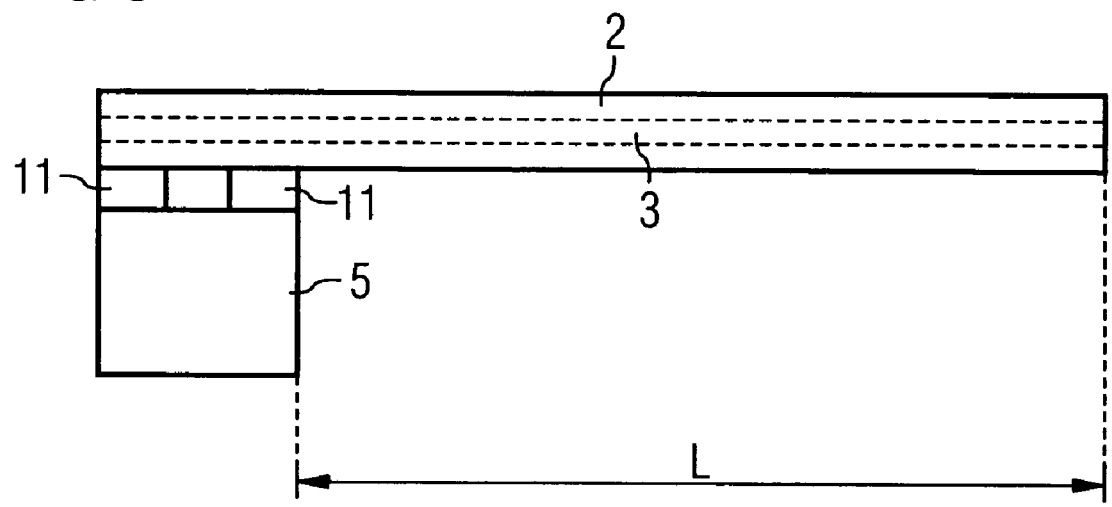
FIG. 3 is a side view of an alternate apparatus for determining a position of a patient during medical examinations.

FIG. 3 shows an alternate apparatus including the tabletop 2, the strain gauge 3 integrated into the tabletop 2, the pedestal 5 on which the tabletop 2 is fastened, and two pedestal sensors 11, which may serve to measure forces acting on the pedestal. The pedestal sensors 11 are capable of measuring the forces on the pedestal 5 that are engendered by the sagging of the tabletop 2. With calibration measurements, a correlation between the sagging of the tabletop, the unsupported length L of the tabletop 2, and the forces acting on the pedestal 5 may be determined. Thus, for each unsupported length L of the tabletop 2, a relationship between the elongation, measured by the strain gauges 3, and thus the sagging of the tabletop 2 and the forces acting on the pedestal 5, which can be measured by the pedestal sensors 11, can be established and stored in memory. As such, after such a calibration, a detection of the elongation of the strain gauges 3 may no longer be needed. Instead, measuring the forces acting on the pedestal 5 via the pedestal sensors 11 may suffice in order to determine the sagging of the tabletop 2. This alternate apparatus is advantageous in that for sensitive imaging methods, in which the strain gauges 3 would interfere with the imaging, the strain gauges 3 need not be integrated into the tabletop 2.

Figure 4:
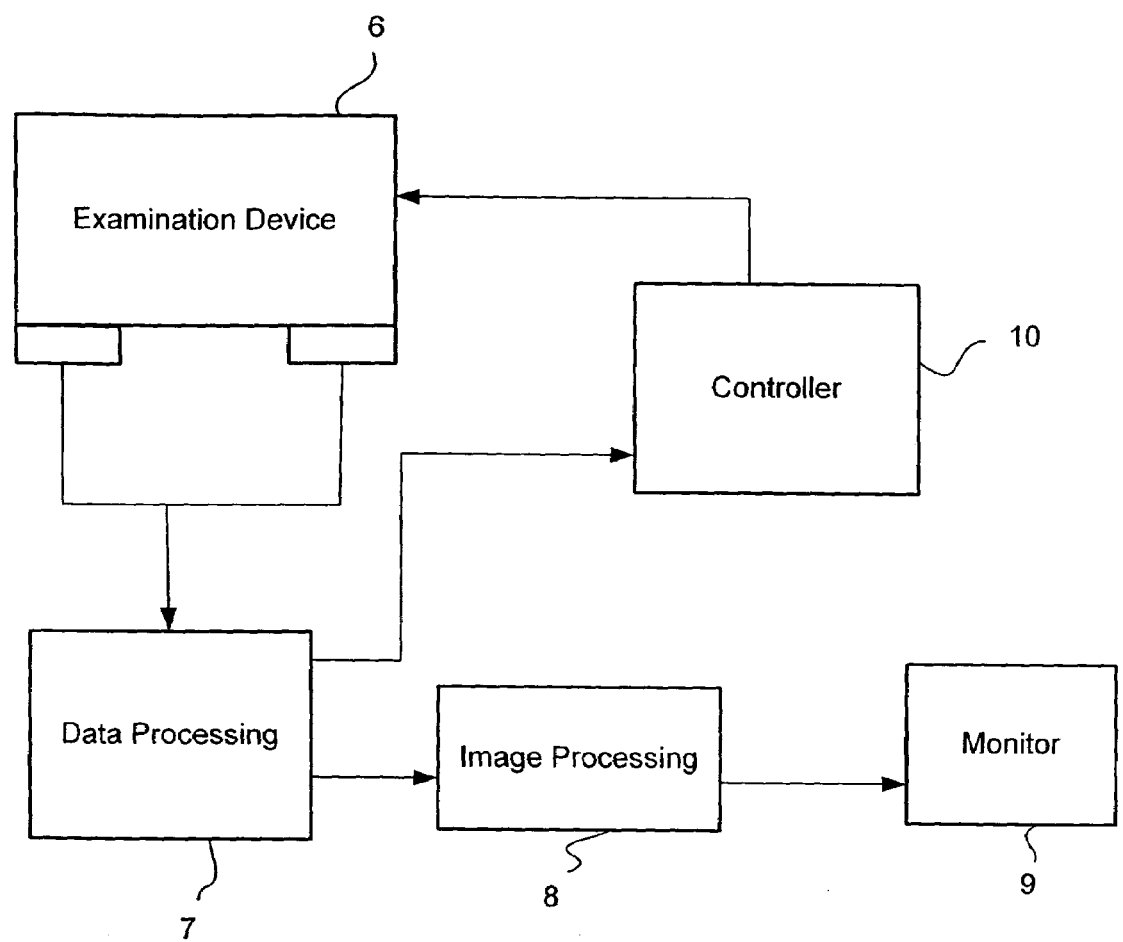
FIG. 4 is a schematic block diagram of a system of the apparatus for determining a position of a patient during medical examinations.

FIG. 4 shows a system utilizing the provided apparatus. An examination device 6 includes the tabletop 2, the pedestal 3, and other devices for the examination, and devices which forward data and are triggered. The examination device 6 can be configured for various examinations, such as MRI, CT, X-ray, mammography, or any other medical examinations. The sensors 4 for measuring the electrical resistance of the strain gauge 3 and/or the pedestal sensors 11 for measuring the forces on the pedestal 5 that are engendered by the sagging are connected to the examination device 6. The sensors 4 and/or the pedestal sensors 11 forward the data to a data processing device 7. In the data processing device 7, the correlation between the data measured by the sensors 4 and the data measured by the pedestal sensors 11 during the calibration is stored in memory. As such, the data processing device 7 can either calculate the sagging on the basis of the data forwarded by the sensors 4, or can calculate the sagging on the basis of the correlation stored in memory as well as the data forwarded by the pedestal sensors 11. If the sagging of the tabletop 2 is on an order of magnitude such that repositioning of the patient 1 or of the imaging device that is part of the examination device 7 is appropriate, then the data processing device 7 can make the appropriate changes in the examination device 6 via a controller 10. The image data forwarded by the examination device 6 are forwarded onward by the data processing device 7 to an image processing device 8, which, after calculations to be made on the basis of the examination method, image processing operations, and correction methods, may show the image on a monitor 9, may output the image as a data file, or may make the image available in alternate ways.

Depending on the examination method implemented, the strain gauge 3, which can be seen or viewed in the images, may be eliminated or removed from these images by processing, filtering or other calculations. This strain gauge removal from the images can be performed either in the data processing device 7 or in the image processing device 8. To avoid such retroactive processing, the method discussed above, in which the forces acting on the pedestal 5 are measured by the pedestal sensors 11, may be implemented so that after the calibration and for the examinations, a use of a tabletop 2, into which the strain gauges 3 are integrated, is no longer needed.

The invention claimed is:

1. An apparatus for determining a position of a patient during medical examinations, the apparatus comprising:
    a tabletop secured to a pedestal, the tabletop operable to support the patient;
    a pedestal sensor operable to detect forces acting on the pedestal due to a bending of the tabletop; and
    a data processing device that is operable to correlate the detected forces acting on the pedestal with a change in length of a removable elongatable strain gauge caused by the bending of the tabletop, a strain gauge sensor being operable to detect the change in length,
    wherein the data processing device is operable to determine a position of the patient based on the correlated forces.

2. The apparatus of claim 1, wherein the at least one elongatable strain gauge is integral to the tabletop in an elongated direction of the tabletop.

3. The apparatus of claim 1, wherein the at least one elongatable strain gauge comprises electrically conductive material.

4. The apparatus of claim 3, wherein a strain gauge sensor is operable to detect the bending as a function of a change in electrical resistance of the at least one elongatable strain gauge.

5. The apparatus of claim 4, wherein the correlation is stored in a memory of the data processing device.

6. The apparatus of claim 5, wherein the data processing device evaluates the bending of the tabletop from data measured by the pedestal sensors and from the correlation stored in memory.

7. The apparatus of claim 4, the data processing device is operable to determine a range of positions of the patient based on the bending detected by the strain gauge sensor.

8. The apparatus of claim 1, wherein the position of the patient includes a distance from a top surface of the tabletop in a resting position to the top surface of the tabletop in a supporting position.

9. A method for determining a position of a patient during medical examinations, the method comprising:
    detecting a bending of a tabletop secured to a pedestal as a function of a change in length of at least one elongatable strain gauge; and
    detecting forces acting on the pedestal due to the bending of the tabletop.

10. The method of claim 9, further comprising:
    integrating the at least one elongatable strain gauge into the tabletop in a elongated direction of the tabletop.

11. The method of claim 9, wherein the at least one elongatable strain gauge comprises electrically conductive material.

12. The method of claim 11, further comprising:
    detecting the change in length of the at least one elongatable strain gauge by measuring a change in electrical resistance of the at least one elongatable strain gauge.

13. The method of claim 9, further comprising:
    mounting a sensor on a longitudinal end of the at least one elongatable strain gauge.

14. The method of claim 13, further comprising:
    evaluating the bending of the tabletop from data measured by the sensor.

15. The method of claim 9, further comprising:
    storing a correlation between the data measured by the sensor and a pedestal sensor in a memory of a data processing device.

16. The method of claim 15, further comprising:
    calculating the bending of the tabletop from the data measured by the pedestal sensor and from the correlation stored in memory.

17. An system for determining a position of a patient during medical examinations, the system comprising:
    a pedestal comprising a pedestal sensor operable to detect a force acting on the pedestal;
    a tabletop secured to the pedestal, the tabletop operable to support the patient; and
    a data processing system comprising:
        a memory that stores a correlation between a sagging of the tabletop and forces acting on the pedestal,
    wherein the data processing system is operable to determine a position of the patient as a function of a force detected by the pedestal sensor and the correlation stored in memory.

18. The system as claimed in claim 17, further comprising at least one elongatable strain gauge integral to the tabletop in an elongated direction of the tabletop.

19. The system as claimed in claim 18, wherein the data processing system is operable to determine the correlation as a function of an elongation of the strain gauge and the detected forces.

* * * * *